United States Patent [19]
Grinblat et al.

[11] Patent Number: 5,725,514
[45] Date of Patent: *Mar. 10, 1998

[54] ADJUSTABLE MINIATURE PANORAMIC ILLUMINATION AND INFUSION SYSTEM FOR RETINAL SURGERY

[75] Inventors: Avi Grinblat, New York; Stanley Chang, Scarsdale, both of N.Y.

[73] Assignee: A.V.I. - Advanced Visual Instruments, Inc., New York, N.Y.

[*] Notice: The term of this patent shall not extend beyond the expiration date of Pat. No. 5,545,153.

[21] Appl. No.: 700,560

[22] Filed: Aug. 8, 1996

Related U.S. Application Data

[63] Continuation-in-part of Ser. No. 290,554, Aug. 15, 1994, Pat. No. 5,545,153.

[51] Int. Cl.$^6$ .............................. A61N 01/30; A61M 35/00
[52] U.S. Cl. .................. 604/294; 604/21; 604/117; 604/174; 606/15; 128/898
[58] Field of Search .......................... 604/20, 21, 117, 604/174, 294; 606/2, 4, 6, 15, 16, 166

[56] References Cited

U.S. PATENT DOCUMENTS

| | | | |
|---|---|---|---|
| 4,820,264 | 4/1989 | Matsui et al. | 604/21 |
| 5,318,560 | 6/1994 | Blount et al. | 606/4 |
| 5,425,730 | 6/1995 | Luloh | 606/15 |
| 5,545,153 | 8/1996 | Grinblat et al. | 604/294 |

Primary Examiner—John G. Weiss
Assistant Examiner—Dennis Ruhl
Attorney, Agent, or Firm—Eliot S. Gerber

[57] ABSTRACT

A medical device and method for eye surgery and method for illumination and fluid flow, particularly retinal surgery, combines a flow of infusing fluid and optical fiber illumination. The device uses a single strand of plastic optical fiber which extends through bores in a juncture device tube and needle cannula with sufficient clearance to permit the flow of the infusing fluid. The illuminating tip of the optical fiber is moved, during surgery, by loosening a cap of the junction device to release the optical fiber, moving the optical fiber within the junction device, and then re-tightening the cap to re-secure the optical fiber.

5 Claims, 5 Drawing Sheets

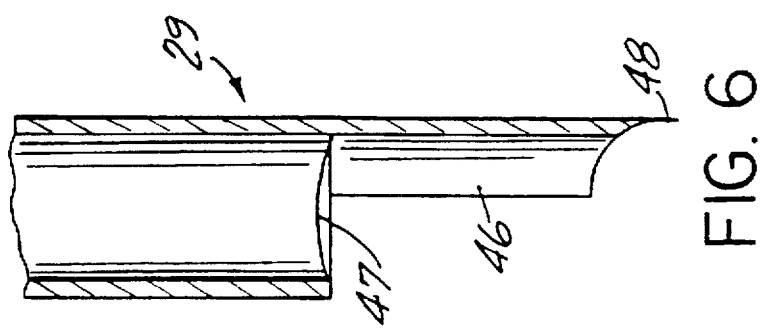
FIG. 6
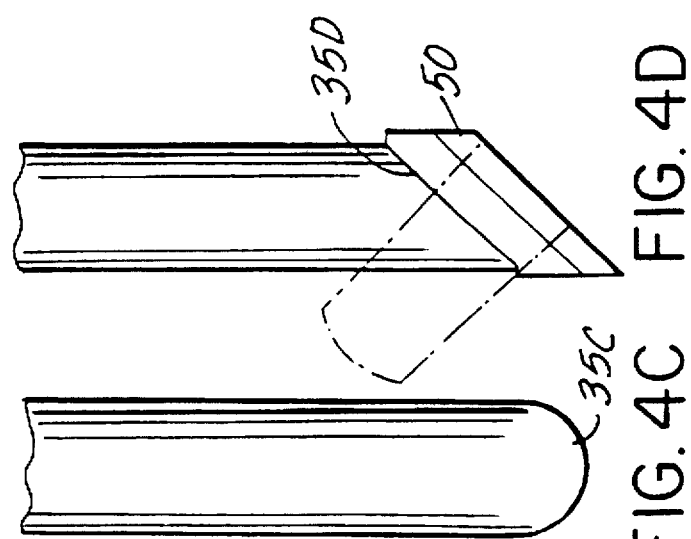
FIG. 4A  FIG. 4B  FIG. 4C  FIG. 4D
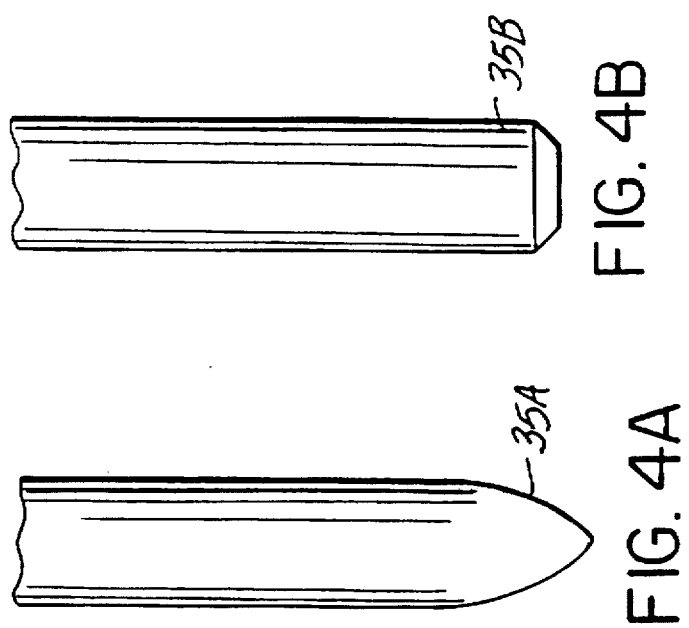
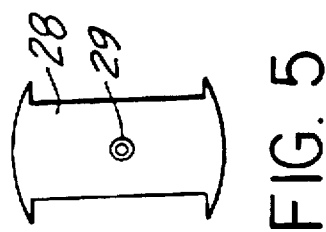
FIG. 5

5,725,514

1
ADJUSTABLE MINIATURE PANORAMIC ILLUMINATION AND INFUSION SYSTEM FOR RETINAL SURGERY

RELATED APPLICATION

This application is a continuation-in-part application partly based on application Ser. No. 08/290,554, filed Aug. 15, 1994, now U.S. Pat. No. 5,545,153, issued Aug. 13, 1996.

FIELD OF THE INVENTION

The present invention relates to medical devices and more particularly a combined source of illumination and fluid infusion for eye surgery, especially opthalmic retinal surgery.

BACKGROUND OF THE INVENTION

At the present time a number of different fiber optic light guides are utilized for eye surgical operations. However, some of these light guides are not suitable for retinal operations as they do not provide sufficient light to the back of the eyeball. In addition, some of the light sources require the eye surgeon to physically hold a light probe, which uses one of his hands and leaves only one hand free for manipulating surgical instruments.

One type of surgical technique involves the use of a suitable fluid, such as saline solution, silicon oil or a gas, which is injected into the eyeball during a surgical procedure to maintain the eye in an inflated state and maintain a uniform pressure in the eye. This technique is called "vitrectomy" and requires a source of fluid, a tube (infusion cannula) leading from the source and a needle cannula connected to the tube and used to inject the fluid into the eyeball. The needle must generally be retained in place during the operation so that the fluid may be constantly replenished.

Often, in the case of retinal surgery (vitrectomy surgery) it is desired that the light source be within the eyeball (within the globe) in the form of an internal light (endoillumination). This permits the direct light of the operating microscope to be turned off and reduces glare at the cornea and corneal contact lens surfaces.

A presently commercially available system for vitro-retinal surgery combining illumination and infusion is the "DPS 100" (TM), from Storz Instrument GmbH, Im Schuhmachergewann 4, D-6900 Heidelberg 1, Germany ("Storz system"). In the Storz system three incisions are made in the eye, each 2.8 mm in length, which allows insertion therethrough of three illuminated pilot tubes each having an outer diameter of 1.65 mm (16 ga.) and an inner bore diameter of 0.9 mm (20 gs.). It is a multiport illumination system having three pilot tubes. The tubes are connected near their ends to plates which are sutured to the pars plana. Very thin instruments, of 20 gauge or less, may be inserted and manipulated through the tubes. A bunch of hair-thin optical fibers are formed, within the pilot tube, into an optical fiber tube whose bore forms the inner diameter of the pilot tube. Each of the tubes transmits light through its bundle of optical fibers and transmits infusion fluids, such as silicon oil, through its bore.

There are a number of disadvantages to the Storz system. First, and primarily, it requires three large incisions, each of 2.8 mm in length, and requires the insertion of three relatively large diameter pilot tubes through the incisions. The number and size of those incisions may be a serious problem in many surgical procedures. Secondly, some surgeons do not wish to be limited to using instruments which fit through the pilot tubes, i.e., instruments of less than 20 gauge. Thirdly, the focused light beam illuminates only a limited area of the retina.

An article entitled "A New Endoillumination Infusion Cannula For Pars Plana Vitrectomy" by K. Zinn, A. Grinblat, H. Katzin, M. Epstein and C. Kot, *Ophthalmic Surgery*, Vol. 11, No. 12, December 1980, pgs. 850–854, incorporated by reference herein, describes a combined illumination and infusion system, which was not manufactured commercially. The infusion cannula (tube for infusion liquids) is within a bundle of optical fibers.

U.S. Pat. Nos. 5,425,730 to Luloh and 4,820,264 to Matsui et al show illuminated cannula systems for vitreous surgery. They do not show a finger-operated means to secure and release an optical fiber so that its tip's position may be changed within the eyeball during the operation.

SUMMARY OF THE INVENTION

In accordance with the present invention a single, relatively thick, preferably 0.50–0.73 mm, optical fiber conducts light from a light source to within the eyeball during eye surgery. The distal end of the optical fiber, which is within the eyeball, is shaped to provide a selected type of illumination. That distal end may be moved further inward toward the rear of the eyeball, or withdrawn, during the operation. The single fiber optic light probe illuminates the entire retina and at the same time the device provides a uniform intraocular pressure in the eye for panoramic vitreretinal surgery. This light probe is preferably, at its tip, shaped like a bullet for diffused wide angle illumination (also termed a "Bullet light").

The optical fiber extends through a cannula needle which is integral with a plate. The cannula is positioned through an incision in the eyeball and the plate is sewn onto it. The cannula transmits fluid, such as saline solution (physiological balanced salt solution), gas or silicon oil, into the eyeball.

A connection tube connects the cannula to a juncture device having a bore therein. An arm of the juncture device is connected to a tube leading to a source of infusion fluid. The body of the juncture device has a cap member secured thereon. An "O" ring within the cap seals the juncture device and is positioned around the optical fiber. The cap member is finger-operated, during surgery, and may be screwed further down on the body (rotation in one direction, for example, clockwise) to increase the pressure of the "O" ring on the optical fiber and secure the optical fiber. It is rotated in the opposite direction, for example, counter-clockwise, to loosen the "O" ring pressure on the optical fiber (unsecure the optical fiber) and thereby permit the user to push it into, or pull it from, the junction device, i.e., change its position in the junction device.

The O.D. (Outer Diameter) of the optical fiber is smaller than the I.D. (Inner Diameter) of the bores of the cannula, connecting tube and juncture device so that the fluid may flow around the optical fiber within those bores.

The illumination and infusion system of the present invention may be used in surgical eye operations in which the surgeon needs both hands to manipulate instruments, for example, in the transplantation of retinal pigment epithelia cell and submacula and subretinal operations.

OBJECTIVES OF THE INVENTION

It is an objective of the present invention to provide a combined fluid infusion and illumination system for eye surgery in which both hands of the surgeon are free to manipulate surgical instruments because the surgeon, or his assistants, need not hold the device in place during the surgical operation.

It is a further objective of the present invention to provide such a system in which the tip free end (distal end) of the optical fiber may be adjusted during surgery, and held in place, to illuminate different internal areas of the eyeball.

It is a further objective of the present invention that at least the portions in contact with the patient's body fluids, namely, the plate and cannula and optical fiber, may be replaced and the remainder of the system may be sterilized, or the entire system may be disposable.

BRIEF DESCRIPTION OF THE DRAWINGS

Other objectives and features of the invention will be apparent from the following detailed description, taken in conjunction with the accompanying drawings.

In the drawings:

FIGS. 4A–4D are enlarged views of alternative free distal tip ends of the optical fiber;

FIG. 5 is a front view of the plate member; and

FIG. 6 is an enlarged cross-sectional view of the cannula portion.

DETAILED DESCRIPTION

Figure 1:
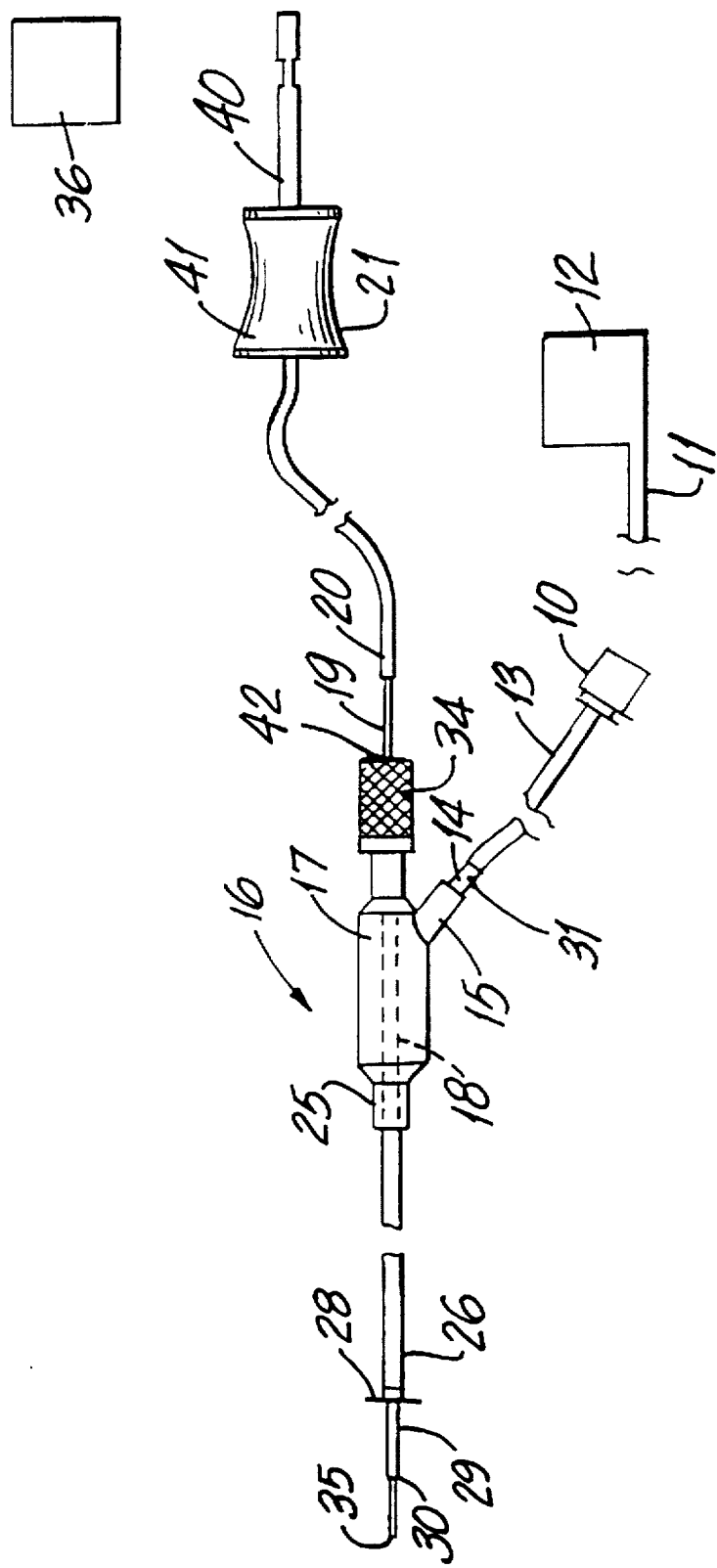
FIG. 1 is a side view of the system of the present invention.

The adjustable miniature panoramic illumination and infusion system for retinal surgery of the present invention is illustrated in FIG. 1. It is especially useful in complicated retinal detachment surgery.

In the human eye the wall of the eye consists of three layers ("tunics") which, from outward to inward, are the fibrous, vascular and sensory tunics. The retina is the sensory tunic and has the form of a cup applied to the inner portion of the choroid. Its sensory layers terminate at the liplike ora serrata. The retina contains light sensitive receptors (visual cells) and impulse carrying nerve cells (neurons). Due to the placement of the retina it is necessary, during surgery, that the illumination cover a wide field, be directed within the eyeball and be directed at the back of the eyeball.

As shown in FIG. 1, a fluid connector 10 is a male connector adapted to mate with a conventional fluid female connector (not shown) for fluid infusion during eye surgery. The tube 11 leads from fluid source 12 to the female connector. A suitable fluid may be a conventional saline solution, silicon oil or perfluorocarbon liquid or perfluorocarbon gases, see Lincoff, H., et al, "The perfluorocarbon gases in the treatment of retinal detachment", *Ophthalmology*, 90:546–551 (1981); Chang, "Low-Viscosity Fluorochemicals in Vitreous Surgery", *Am. Jnl. Ophthalmol.*, 103:38–43 (1987); Chang et al, "Controlled Delivery of Perfluorocarbon Liquids", *Am. Jnl. Ophthalmol.*, 107:299–300, 1989; the three articles being incorporated by reference.

The male fluid connector 10 has a bore and is attached to fluid conduction tube (cannula) 13, which is preferably 22 cm. in length. The end 14 of tube 13 is connected, by a metal band, to the arm 15 of the junction device 16, shown in enlarged drawing FIG. 2. The body portion 17 of junction device 16 has a bore 18 through which a single optical fiber 19 extends.

Preferably the optical fiber 19 is a plastic optical fiber having preferably an outer diameter of 0.5 mm. (small model) or alternatively an O.D. of 0.73–0.75 mm (larger model).

An optical fiber generally consists of a solid core, which may be transparent glass or plastic of a higher refractive index, and a very thin cladding surrounding the core, the cladding being a transparent material of a lower refractive index The optical fiber is covered with a protective sheath which surrounds the outer cladding. In the case of plastic optical fiber, the protective sheath may be relatively thick compared to the optical fiber. Preferably the plastic optical fiber is free to slide within its protective sheath.

Plastic optical fibers, due to their flexibility and relatively low cost, are preferable. Generally plastic optical fibers are formed of a transparent synthetic resin-based material, for example, polystyrene and resins, such as polymethylmethacrylate. Examples of such resins are given in U.S. Pat. No 4,778,245, incorporated by reference. Generally the core is polystyrene based and has an acrylic based cladding, or the core is acrylic based and has a cladding of fluorinated PMMA-acrylic.

The single thick optical fiber 19 (light pipe), consisting of a core and its cladding, is covered by a black plastic tubular sheath 20 having an outer diameter (O.D.), for example, of 2.0 mm, which leads from junction device 16 to a conventional light male connector 21. The connector 21 fits into a female light connector of a standard high intensity light source 36, such as a zenon or halogen bulb in an enclosure. The connector 21 is a one-piece aluminum member.

The junction device 16, which preferably is injection-molded of plastic, has a front tubular nose portion 25 which fits inside the inner end of flexible tube (cannula) 26. The tube 26 is preferably 20 mm O.D. and 12 cm. long. The outer end 27 of the tube 26 fits tightly on a plate member 28 having a hole therethrough, the hole leading to an integral extending tubular cannula (needle) portion 29. The plate member 28 is adapted to be removably sewn to the eyeball (fibrous tunic) at the start of the operation. Preferably the cannula portion 23 is 0.9 mm. O.D., 4.0 mm. in length, or in the range 3.5–6.0 mm, and has a bore of 0.75 mm I.D. (Inner Diameter) and 0.9 mm O.D. for an optical fiber of 0.5 mm O.D. (small model) and a bore of 0.95 I.D. and 1.1 mm O.D. for the larger model having an optical fiber of 0.73–0.74 O.D. The optical fiber 19 fits through and extends beyond the free end point 30 of the cannula portion 29. There is sufficient room between the outer diameter of the fiber optic and the inner diameter of the tube 26 and the outer diameter of the fiber optic and the inner diameter of the cannula portion 29 for the free flow of the infusion fluid.

Figure 2:
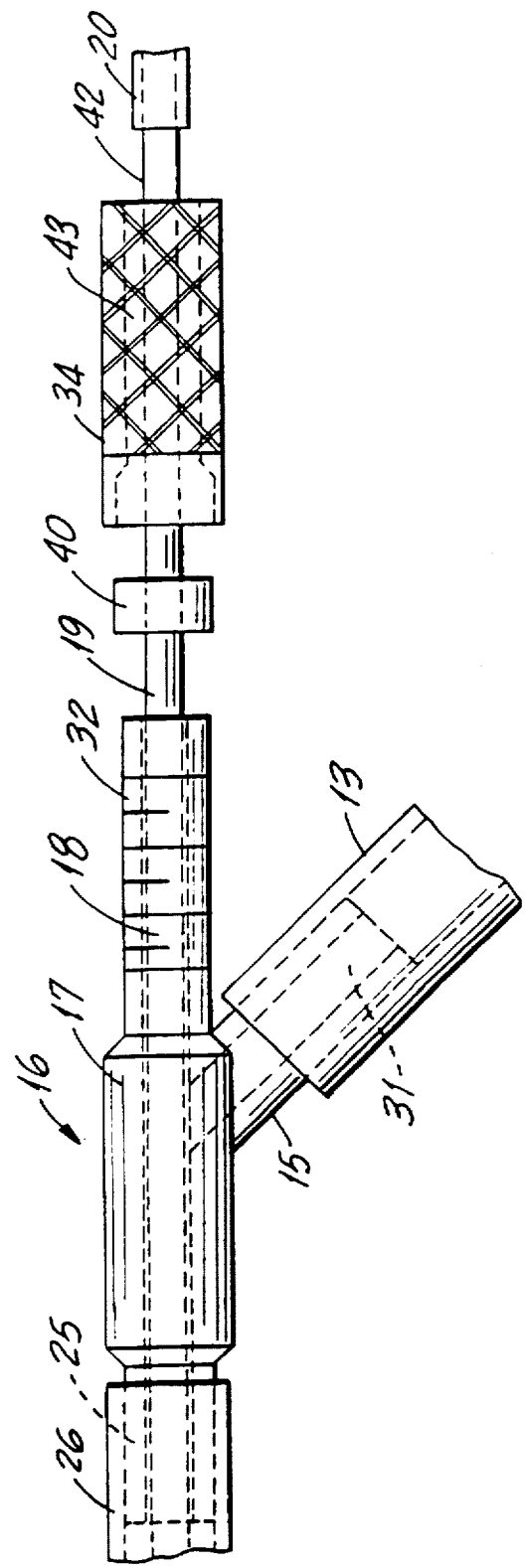
FIG. 2 is an enlarged exploded side view of the juncture device of the present invention.
Figure 3A:
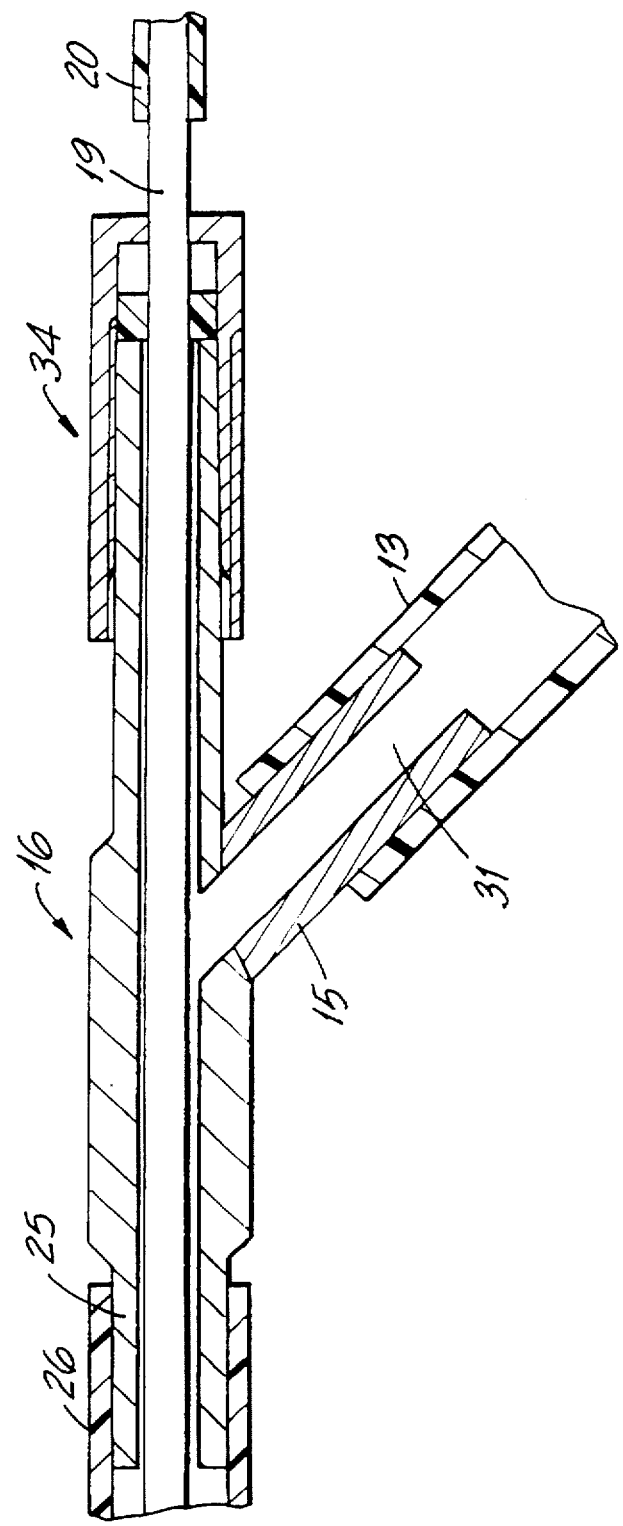
FIG. 3A is a side cross-sectional view of the juncture device as shown in FIG. 2.
Figure 3B:
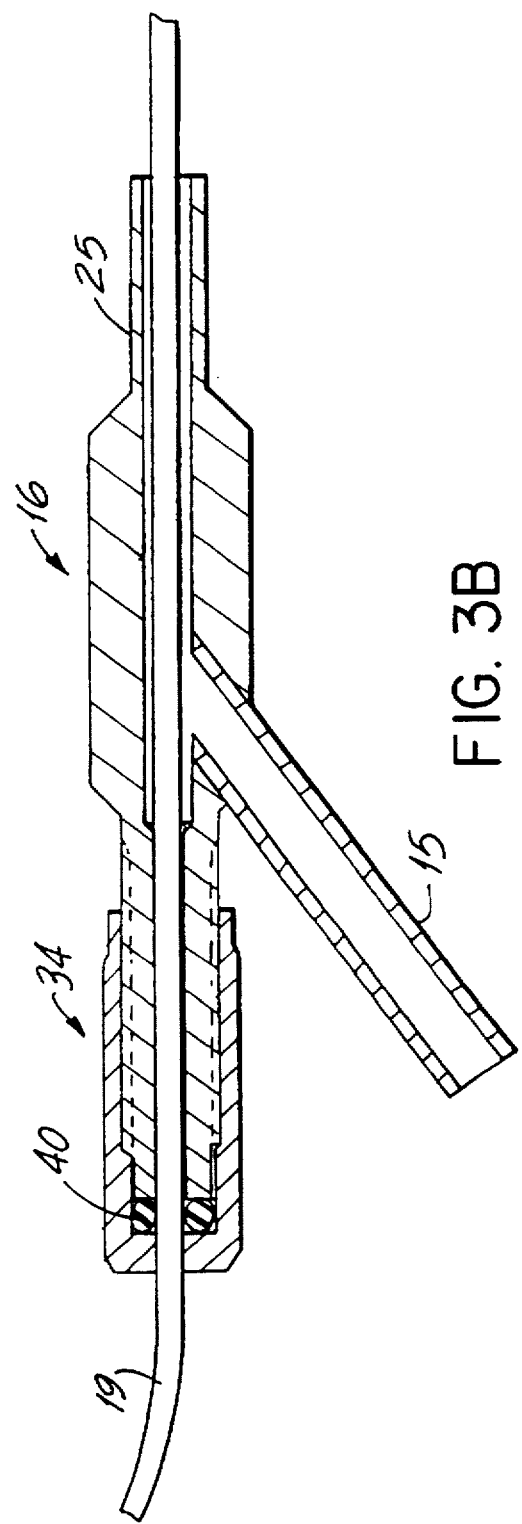
FIG. 3B is a side cross-sectional view of an alternative juncture device using a round cross-sectional "O" ring.

As shown in FIG. 2, the bore 31 of the arm portion 15 leads to the bore 18 of the body portion 17 and conducts infusion fluid thereto. The rear end of the body portion 17 has external screw threads 32 which mate with the internal screw threads of nut cap member 34. An "O" ring 40 of a suitable resilient silicon plastic is a ring having a flat, or round, outer surface and an I.D. which is the same 0.5 or 0.73–0.75 as the O.D. of the optical fiber. The ring 40 fits over the optical fiber 19 and is within the cap member 34.

When the cap member 34 is tightened down onto the body portion 17, the "O" ring 40 is squeezed about the optical fiber 19 and forms a fluid-tight seal. When so tightened (secured), the optical fiber 19 cannot be moved forward or backwards.

However, the free end 35 of the optical fiber 19 may be adjusted forward or backwards, relative to the end 30 of the cannula portion 29, by loosening cap member 34, unsecuring the optical fiber, and pushing, or pulling, the optical fiber 19. The surgeon loosens (counter-clockwise rotation) or tightens (clockwise direction) cap member 34, preferably having a ring of protrusions thereon, by using his/her fingers, without using a screw driver or other tool. This adjustment permits the surgeon to exactly locate, and re-locate, the optical fiber end 35 within the eyeball during the operation. The cap and "O" ring constitute a finger-operable optical securing means.

As shown in FIG. 2, the junction device 16 has a body portion 17 having an O.D. of 50 mm and is 2.5 cm. long. Its arm portion 15 is 70 mm long and has an O.D. of 20 mm. The bore 18 is 0.6 or 0.78 mm I.D. The cap member is 9.0 mm. long and has a knurled surface and an O.D. of 3.0 mm. The orifice 42 in the end of the cap member, through which the optical fiber extends, is 0.7 mm for the small model and 0.95 mm for the larger model. The external thread extends for 8.0 mm. and the bore 43 is 0.78 mm I.D., the bore 43 being an extension of the bore 18.

As shown in FIG. 5, a front view of the plate member 28, it is 3.0 mm wide (at its center). All of the metal portions of the device are preferably made of surgical grade stainless steel.

It will be understood that the dimensions set forth above constitute a preferred example of the present invention and that modifications may be made therein.

As shown in FIG. 4A, the distal end (tip or free end) of the optical fiber may be formed as a rounded cone 35A. In FIG. 4B it is formed with a flat end 35B having bevels, to provide a wide angle of illumination. In FIG. 4C it is formed with a rounded end 35C to provide a wide angle of illumination with a smaller reflection level, compared to the shape of FIG. 4B. In FIG. 4D it is formed with a flat and angled face having a polished tip 35D. A miniature mirror 50, preferably a front surface silver coating, may be positioned to reflect the light at a selected angle.

As shown in FIG. 6 the cannula portion 29 has a bore 45 whose I.D. is 0.95 mm for a 0.75 mm optical fiber or 0.75 mm for a 0.5 mm optical fiber. It has an extending cover (lip) 46 which shields the light from the optical fiber. The distal tip of the optical fiber may be positioned so that it extends beyond the orifice 47 and is back of the cannula portion tip 48.

What is claimed is:

1. An illuminating and infusion system used in connection with eyeball surgery, comprising:

(a) a fluid conduction tube to be connected to a source of infusion fluid;

(b) a single optical fiber having an outer diameter and a proximal end adapted to be connected to a source of light at the proximal end and having a free opposite distal end, said distal end adapted to provide illumination within an eyeball during the eye surgery;

(c) a juncture device having a bore therethrough with an inner diameter, the fluid conduction tube being connected to the juncture device to conduct the infusion fluid to the juncture device bore;

(d) a plate adapted to be removably attached to the eyeball during surgery and a needle cannula fixed to the plate, the needle cannula having a bore with an inner diameter and having a free distal end;

(e) a connecting tube having a bore and connected between the needle cannula and the juncture device; the connecting tube being an elongated and flexible tube;

(f) the optical fiber being within the bores of the juncture device, the connecting tube and the needle cannula and the distal end of the optical fiber adapted to illuminate beyond the free distal end of the needle cannula, the outer diameter of the optical fiber being smaller than the inner diameter of the juncture bore, and needle cannula bore thereby permitting infusing fluid to flow around the optical fiber within the bores; and (g) finger-operable optical fiber securing means on the juncture device to secure the optical fiber and to permit changing the position of the optical fiber within the juncture device by finger non-tool operation by the user during the surgery while the plate remains attached to the eyeball and thereby permitting adjustment of the position of the distal end of the optical fiber relative to the distal end of the needle cannula.

2. A system as in claim 1 wherein the juncture device of (c) includes a finger-operable cap member which is rotatable in one direction to secure the optical fiber and rotatable in an opposite direction to unsecure the optical fiber and thereby permit the user to change the position of the optical fiber within the juncture device when the optical fiber is unsecured.

3. A system as in claim 2 wherein the cap member is a cap of the juncture device having a hole through which the optical fiber protrudes.

4. A method of illuminating and infusing the eyeball during eye surgery, comprising:

(a) connecting a fluid conduction tube to a source of infusion fluid and flowing infusion fluid therethrough;

(b) connecting a single optical fiber having an outer diameter and a proximal end to a source of light at the proximal end, the optical fiber having a free opposite distal end adapted to provide illumination within the eyeball during the eye surgery;

(c) connecting the fluid conduction tube to a juncture device, the juncture device having a bore therethrough with an inner diameter; wherein the juncture device includes a body portion and an optical fiber securing means which is finger-operated without tools;

(d) removably attaching a metal plate to the eyeball during the surgery, the plate having a needle cannula which is metal and integral with the plate and has a bore with an inner diameter, the needle cannula having a free end;

(e) wherein a connecting tube has a bore and is connected between the needle cannula and the juncture device;

(f) the optical fiber is within the bores of the juncture device, the connecting tube and the needle cannula and the distal end of the optical fiber illuminates beyond the distal free end of the needle, the outer diameter of the optical fiber is smaller than the inner diameter of the juncture device bore; and (g) during the eye surgery, operating the optical fiber securing means using only fingers to loosen the optical fiber and then moving the optical fiber within the juncture device and thereby moving the distal end of the optical fiber relative to the free end of the needle, and then using only fingers operating the optical fiber securing means to secure the optical fiber against movement within the juncture device.

5. A method as in claim 4 wherein the operation of the optical fiber securing means is the rotation and counter-rotation of a cap to secure and unsecure the optical fiber.

* * * * *